US005719045A

United States Patent [19]

Heveling et al.

[11] Patent Number: 5,719,045
[45] Date of Patent: Feb. 17, 1998

[54] PROCESS FOR PREPARING NICOTINAMIDE

[75] Inventors: Josef Heveling; Erich Armbruster, both of Naters; Lukas Utiger, Termen; Markus Rohner, Kourim; Hans-Rudolf Dettwiler; Roderick J. Chuck, both of Brig-Glis, all of Switzerland

[73] Assignee: Lonza AG, Gampel/Valais, Switzerland

[21] Appl. No.: 741,806

[22] Filed: Oct. 31, 1996

[30] Foreign Application Priority Data

Nov. 1, 1995 [CH] Switzerland ............... 3090/95

[51] Int. Cl.$^6$ ................................................ C12P 17/12
[52] U.S. Cl. .................. 435/122; 435/129; 435/170; 435/252.1
[58] Field of Search ................. 435/122, 129, 435/170, 252.1

[56] References Cited

U.S. PATENT DOCUMENTS 5,179,014 1/1993 Watanabe et al. ............... 435/129
5,258,305 11/1993 Yamada et al. ................... 435/280
5,334,519 8/1994 Yamada et al. ................... 435/129

FOREIGN PATENT DOCUMENTS

| 0188316 | 8/1986 | European Pat. Off. |
| 0307926 | 3/1989 | European Pat. Off. |
| WO 94/22824 | 10/1994 | WIPO |
| WO 95/32055 | 11/1995 | WIPO |

OTHER PUBLICATIONS

Ullmann's *Encyklopädie der technischen Chemie*, 4th edition, vol. 23, pp. 708 ff.
Ullmann's *Encyklopädie der technischen Chemie*, 4th edition, vol. 19, pp. 602 ff.

*Primary Examiner*—Herbert J. Lilling
*Attorney, Agent, or Firm*—Fisher, Christen & Sabol

[57] ABSTRACT

A process for preparing nicotinamide, wherein, in the first stage, 2-methyl-1,5-diaminopentane is catalytically converted into 3-picoline, then the 3-picoline is converted via an ammonoxidation into 3-cyanopyridine and, finally, the 3-cyanopyridine is converted microbiologically into the nicotinamide.

26 Claims, No Drawings

PROCESS FOR PREPARING NICOTINAMIDE

BACKGROUND OF THE INVENTION

1. Field of the Invention

The invention relates to a new process for preparing nicotinamide.

2. Background Art

Numerous processes are known for the preparation of nicotinamide, which is one of the B-group vitamins essential to man and beast. Essentially only two processes have achieved industrial importance, namely, the nitric acid oxidation of alkylpyridines and the ammonoxidation of alkylpyridines (cf. *Ullmann's Encyklopädie der technischen Chemie*, 4th edition, Vol. 23, pp. 708 ff. and Vol. 19, pp. 602 ff.).

Although the nitric acid oxidation, specifically of 2-methyl-5-ethylpyridine, is a very selective process, it incorporates a risk potential for the minimization of which highly qualified personnel, optimum infrastructure and a high standard of know-how are indispensable prerequisites. Such process of nitric acid oxidation is, therefore, unsuitable for technology transfer, for example to places where the prerequisites mentioned can only be realized in part.

The ammonoxidation, specifically of 3-picoline, has not previously come close to the industrial importance of the nitric acid oxidation, although numerous publications describe quantitative conversions with yields of over 90 percent (cf. *Ullmann's Encyklopädie der technischen Chemie*, 4th Edition, Vol. 19, pp. 602 ff.). Essential prerequisites for an industrially usable catalyst are not only its degree of conversion and its selectivity, but likewise are the achievable space velocity over the catalyst (amount of starting material/catalyst volume/time=kg $l^{-1}h^{-1}$) and its operating life. Particularly in respect of the last two criteria, the known ammonoxidation catalysts from the prior art are not satisfactory.

BROAD DESCRIPTION OF THE INVENTION

An object of the invention is to provide an industrially usable process which, on the one hand, is based on a technology which is relatively simple to master and, on the other hand, meets all of the criteria and requirements of an economical process. Other objects and advantages of the invention are set out herein or are obvious herefrom to one skilled in the art.

The objects and advantages of the invention are achieved by the process of the invention.

According to the process of the invention for preparing nicotinamide, In the first stage:

(a) 2-methyl-1,5-diaminopentane in the gas phase at 300° to 400° C. and at 0 to 10 bar gauge pressure is converted into 3-methylpiperidine by passing it over a catalyst containing as the active component at least one oxide of Al and/or Si, having at the surface a ratio of acid centers to basic centers of more than 2 and having a specific surface area of more than 40 m²/g, and, immediately afterwards, the 3-methylpiperidine is passed at 220° to 400° C. over a dehydrogenation catalyst and is converted into 3-picoline, then in the second stage:

(b) 3-picoline is, in the presence of ammonia and an oxygen-containing gas, passed at 280° to 400° C. over an ammonoxidation catalyst comprising the oxides of vanadium, titanium, zirconium and molybdenum in a molar ratio of $V_2O_5$ to $TiO_2$ to $ZrO_2$ of from 1:1:2, respectively, to 1:12:25, respectively, and having an $MoO_3$ content, based on the $V_2O_5$, of from 0.54 percent by weight to 2.6 percent by weight, and, finally, in the third stage:

(c) the resultant 3-cyanopyridine is converted by means of microorganisms of the genus Rhodococcus into the end product.

DETAILED DESCRIPTION OF THE INVENTION

The first process stage, viz. the preparation of 3-picoline from 2-methyl-1,5-diaminopentane, is comprehensively described in (a) PCT Published Application WO 94/22824, and (b) U.S. patent application Ser. No. 08/525,744.

U.S. patent application Ser. No. 08/525,744, applicants: Josef Heveling, et al., entitled: "Process For The Preparation Of 3-Methylpiperidine and 3-Methylpiperidine and 3-Methyl Pyridine by catalytic cyclization of 2-methyl-1,5-Diaminopentane", filed on Oct. 2, 1995, is commonly owned with this application. The pertinent portions of U.S. patent application Ser. No. 08/525,744 are incorporated herein by reference.

U.S. patent application Ser. No. 08/525,744 discloses a process for the preparation of 3-methylpyridine (that is, 3-picoline), wherein, first, 3-methylpiperidine is prepared from 2-methyl-1,5-diaminopentane in the gas phase at 300° to 400° C. and at 0 to 10 bar above atmospheric by passing the starting material over a catalyst which contains, as the active component, at least one oxide of Al and/or Si, which has a ratio between acid and basic centers on the surface of greater than 2 and has a specific surface area of greater than 40 m²/g, and the resultant 3-methylpiperidine is subsequently passed over a dehydrogenation catalyst, preferably at 220° to 400° C. The dehydrogenation catalyst used is a noble metal, such as, palladium or platinum, on a support. The dehydrogenation catalyst preferably is palladium on an amorphous silicon/aluminum oxide which has been prepared by ion exchange with a soluble palladium complex.

The term "oxides of Al and/or Si" is taken to mean the individual oxides, such as $Al_2O_3$, mixed oxides of $Al_2O_3/SiO_2$ and crystallized compounds thereof, such as aluminum silicates, in particular zeolites. It is important that they have a predominantly acidic character and a specific surface area of greater than 40 m²g. The acidic character arises from the ratio between acidic and basic centers on the surface, which must, in accordance with the invention, be greater than 2. The acidic centers are determined analytically by irreversible adsorption of $NH_3$ at 80° C., and the basic centers by irreversible adsorption of $CO_2$ at 80° C. Preferred catalysts for the novel process are activated $Al_2O_3$, mixed oxides of $Al_2O_3/SiO_2$, or zeolites. Zeolites are crystalline natural or synthetic aluminum silicates which have a highly ordered structure with a rigid three-dimensional network of $SiO_4$ and $AlO_4$ tetrahedra connected by common oxygen atoms. The ratio between the number of Si and Al atoms and oxygen is 1:2. The electrovalence of the aluminum-containing tetrahedra is compensated by inclusion of cations in the crystal, for example, alkali metal or hydrogen ions. Cation exchange is possible. The spaces between the tetrahedra are occupied by water molecules before dehydration by drying or calcination.

If the zeolite, owing to its preparation method, is not in the catalytically active, acidic H form, but instead, for example, in the Na form, it can be converted fully or partially into the desired H form by ion exchange, for example with ammonium ions, followed by calcination or by treatment with acids.

The catalysts are preferably employed as fixed-bed catalysts, and the starting material is expediently passed through the catalyst using hydrogen or an inert gas, such as nitrogen, as carrier gas.

The reaction temperature is set at 300° to 400° C., preferably at 305° to 375° C. The pressure is 0 to 10 bar, preferably 0 to 5 bar, above atmospheric.

A measure of the flow rate over catalysts is the mass hourly space velocity (MHSV). In the present case, an MHSV of 2.1 to 4.2 g of starting material per g of catalyst and per hour is advantageously maintained. The vapor-form starting material can be diluted, preferably with $N_2$ or $H_2$.

3-Methylpiperidine can be converted into 3-picoline by known dehydrogenation processes. The 3-methylpiperidine stream produced by the process of the invention can be passed directly over a dehydrogenation catalyst, so that the dehydrogenation takes place immediately after the cyclization. This is possible because the 3-methylpiperidine is produced in unusually high purity and in particular now contains virtually no MPDA, which has been found greatly to impair the activity of dehydrogenation catalysts.

The dehydrogenation catalysts used are preferably noble metals, such as, for example, Pd or Pt, on a support. Particularly advantageous dehydrogenation catalysts have been found to be those obtainable from amorphous silicon aluminum oxides by ion exchange with soluble palladium complexes, such as $[Pd(NH_3)_4]Cl_2$. The amorphous silicon aluminum oxides are advantageously first dewatered and charged with ammonia. The ion exchange with the soluble palladium complex can take place by suspension of the amorphous oxide in a solution of the complex. Alternatively, a solution of the complex can be passed through a packing of the amorphous oxide, but, in contrast to the former method, uniform loading can only be achieved by complete exchange.

The above methods also allow palladium contents of up to 5 percent by weight or more to be achieved in one step using relatively dilute solutions, for example, 0.01 mol/l of $[Pd(NH_3)_4]Cl_2$.

The reaction temperature during the dehydrogenation is preferably 220° to 400° C. In one embodiment, the cyclization catalyst is applied directly to the dehydrogenation catalyst bed, and the 2-methyl-1,5-diaminopentane is passed in from above. In a preferred embodiment, the catalysts are introduced into separate reactors. This allows independent temperature control and, if desired, independent catalyst regeneration.

The 3-picoline obtained can, without intermediate purification, be fed directly to the ammonoxidation stage. However, it is preferably subjected to, for example, an intermediate purification by distillation, which has a positive effect on the catalyst life in the next (second) stage.

The ammonoxidation in the second stage is the subject-matter of (a) PCT Published Application WO 95/32055 (PCT/EP 95/0 1945) and (b) U.S. patent application Ser. No. 08/732,343. U.S. patent application Ser. No 08/732,343, applicants: SEMBAEV et at., entitled: "Catalytic Composition For The Oxidative Ammonolysis Of Alkylpyridines", filed on the same date as this application, is commonly owned with this application. The pertinent portions of U.S. patent application Ser. No. 08/732,343 are incorporated herein by reference.

U.S. patent application Ser. No. 08/732,343 discloses a catalyst composition of the oxides of vanadium, titanium, zirconium and molybdenum, for use in the oxidative ammonolysis of alkylpyridines, for example, 3-methylpyridine to the corresponding 3-cyanopyridine.

As the ammonoxidation catalyst, preference is given to using a catalyst composition comprising the oxides of vanadium, titanium, zirconium and molybdenum in a molar ratio of $V_2O_5$ to $TiO_2$ to $ZrO_2$ of from 1:3:4, respectively, to 1:8:16, respectively, and having a $MoO_3$ content, based on $V_2O_5$, of from 0.54 percent by weight to 1.20 percent by weight. The preparation of the catalyst is comprehensively described in the above-mentioned PCT application PCT/EP 95/01945.

As the oxygen-containing gas, preference is given to using air since air has the advantage that the oxygen is already diluted with inert gases. However, the partial pressure of oxygen can be further regulated by mixing in inert gas such as nitrogen or oxygen-free process gases obtained by recycling.

The reactants 3-picoline, ammonia and oxygen-containing gas (calculated as $O_2$) are advantageously passed in gas form and in a molar ratio of from 1:1:1.5, respectively, to 1:8.5:60, respectively, at 280° to 400° C., preferably 310° to 380° C., over the catalyst. The preferred molar composition of the feed gas is 3-picoline, ammonia and oxygen-containing gas (calculated as $O_2$) in a ratio of from 1:1:1.5, respectively, to 1:4:25, respectively.

Water can have a favorable influence on the activity of the catalyst and is advantageously passed over the catalyst in a molar ratio of water to 3-picoline of up to, and including, 5:1, respectively, and preferably about 1.5:1, respectively.

In this second stage, yields of 3-cyanopyridine of up to 99 percent are achieved at a space velocity over the catalyst of from 50 to 150 (gl-$^{-1}$h$^{-1}$) of 3-picoline. The catalyst life is likewise extraordinarily high and is at least one year.

As compared with the prior art, the present ammonoxidation process, as a constituent part of the process of the invention, made it possible to develop a process which satisfies all of the criteria of an industrial reaction.

The resultant 3-cyanopyridine can be fed to the biohydrolysis in the form of an aqueous solution, either directly or after a work-up step, e.g., a crystallization, extraction or distillation. A preferred work-up comprises countercurrent extraction of the 3-cyanopyridine with toluene, for example, and subsequent vacuum distillation. The solvent used, e.g., toluene, can be completely recycled.

The biohydrolysis of 3-cyanopyridine as substrate to give nicotinamide is advantageously carried out using microorganisms of the species *Rhodococcas rhodochrous, Rhodococcus sp. S - 6* or *Rhodococas equi*, preferably using microorganisms of the species *Rhodococcus sp. S - 6* (FERM BP-687), *Rhodococas rhodochrous J1* (FERM BP-1478) or *Rhodococcus equi* TG328 (FERM BP-3791). In particular, the reaction is carried out by means of microorganisms of the species *Rhodococcus rhodochrous* (FERM BP-1478). The three species mentioned above were deposited by Nitto Chemical Industry Co., Ltd. in the Fermentation Research Institute, Agency of Industrial Science & Technology, Ministry of International Trade and Industry, Japan, according to the rules of the Budapest Treaty. The FERM BP-numbers are the official deposit numbers. The microorganisms of the species *Rhodococcus sp. S - 6, Rhoclococcus rhodochrous J1* and *Rhodococcus equi* TG328 are microorganisms described in the literature. *Rhodocoous rhodochrous J1*(FERM BP-1478) is comprehensively described in (a) European Published Patent Application No. B 307,926, and (b) U.S. Pat. No. 5,334,519, *Rhodococcus sp. S - 6* (FERM BP-687) in (a) European Published Patent Application No. A 0,188,316 and (b) U.S. Pat. No. 5,179,014, and and *Rhodococcus equi* TG328 (FERM BP-379 1) in U.S. Pat. No. 5,258,305.

The pertinent portions of U.S. Pat. No. 5,179,014 are incorporated herein by reference. U.S. Pat. No. 5,179,014 discloses and described *Rhodococcus sp.* S - 6, and its morphology, growth state in various culture media (30° C.), physiological characteristics and chemical composition of cells.

The pertinent portions of U.S. Pat. No. 5,334,519 are incorporated herein by reference. U.S. Pat. No. 5,334,519 discloses and describes *Rhodococcus rhodochrous sp.* J - 1, and its morphology.

The pertinent portions of U.S. Pat. No. 5,258,305 are incorporated herein by reference. U.S. Pat. No. 5,258,305 discloses and describes *Rhodococcus equi* TG328, and its morphology, growth on culture media (at 30° C.) and physiological properties.

Likewise suitable for the process are the functionally equivalent variants and routants of these microorganisms. For the purposes of the present invention, "functionally equivalent variants and mutants" are microorganisms which have essentially the same properties and functions as the original microorganisms. Such variants and mutants can arise by chance, for example, by means of UV irradiation.

The microorganisms are usually cultured (grown) and the effective enzymes induced prior to the actual biotransformation as described in European Published Patent Application No. B 307,928. The biotransformation is preferably carried out using, as is customary in the art, immobilized microorganism cells.

The biotransformation is advantageously carried out in a pH range of from 6 to 10, preferably in a pH range of from 6.5 to 8.5. The pH is here advantageously set using a suitable phosphate buffer.

The biotransformation can be carried out at a temperature of from 5° to 50° C., preferably from 15° to 30° C.

Preferably, the biohydrolysis of the 3-cyanopyridine, which is advantageously present in aqueous solution in a concentration of from 5 to 30 percent by weight, is carried out in a reactor cascade comprising from 2 to 5 connected stirred reactors which each contain the biocatalyst. Particular preference is given to using cascades comprising 3 or 4 stirred vessels. The 3-cyanaopyridine content of the aqueous solution particularly preferably fluctuates between 10 and 20 percent by weight.

After a residence time of from 5 to 30 hours, the nicotinamide can be isolated from the product stream, for example, by crystallization. Preferably, the reaction solution is purified over activated carbon or a polystyrene resin (e.g., Amberlite) and the nicotinamide is isolated from the aqueous phase in a conventional manner.

The conversion in the biohydrolysis is virtually quantitative and gives a nicotinamide having a purity of over 99.5 percent.

The most preferred embodiments of the invention are set out in the following examples.

EXAMPLE 1a

MPDA (methytdiaminopentane) to 3-picoline

A reactor (13 mm φ) was charged with 4 g of a Pd catalyst (1% Pd/$Al_2O_3$) and, on top of that, 3 g of H-ZSM-5 [54.5% of pentasil (Si/Al=18) plus 45.5% of binder]. (The starting material was always fed into the reactor from the top.) The reaction conditions were: temperature: 305° to 320° C., 15 ml/min of $N_2$, and pressure: 5 bar. In a temperature range of 305° to 320° C. and at an MHSV (mass hourly space velocity over the catalyst) of 0.6 g/ (g·h), yields of up to 97 percent of 3-picoline were achieved, with the only further product found being 2.9 percent of MPI (methylpiperadine). Thus, complete conversion of the MPDA to desired products took place. No deactivation of the catalysts were observed over a period of 10 days. $H_2$ can be used as the carrier gas in place of $N_2$.

EXAMPLE 1b

Preparation of 3-picoline Using Two Separate Reactors and Commercial MPDA (MPDA to 3-picoline in 2 Stages With Isolation of MPI)

1st Stage: A reactor (13 mm φ) was charged with 3 g of ZSM-5 in the ammonium form (particle size: 0.5 to 1 mm). MPDA was vaporized and, together with a carrier gas stream of 15 ml/minute of $N_2$, was passed at a pressure of 5 bar and a temperature of 335° C. over the catalyst. The MHSV was 4.2 g of MPDA per gram of catalyst per hour. The MPDA used was a commercial product obtainable from DuPont de Nemours under the trade name Dytek A. The experiment ran for 280 hours. A deactivation of the catalyst was not observed. The product was condensed and the ammonia formed was able to escape. The yields of MPI were virtually quantitative (>99.5 percent).

2nd Stage: A reactor (13 mm φ) was charged with 10 g of a Pd-$MgCl_2$/$Al_2O_3$ dehydrogenation catalyst. The MPI from the first stage was passed in vapor form together with a carrier gas stream of 15 ml/minute of $N_2$ at a pressure of 1 bar and a temperature of 280° C. over the catalyst. The MHSV was 0.23 g of MPI per gram of catalyst per hour. The experiment ran for 190 hours. A deactivation of the catalyst was not observed. After 190 hours, the following product composition was determined by gas chromatography: 99.3 percent of 3-picoline, and 0.4 percent of MPI.

EXAMPLE 1c

Preparation of 3-picoline Using Two Separate Reactors and Commercial MPDA (MPDA to 3-picoline in 2 Stages Without Isolation of MPI)

A reactor (13 mm φ) was charged with 3 g of $NH_4$-ZSM-5 (particle size: 0.5 to 1 mm). MPDA was vaporized and, together with a carrier gas stream of 15 ml/minute of $N_2$, passed at a pressure of about 1 bar and a temperature of 320° C. over the catalyst. The MHSV was between 1 and 2 g of MPDA per gram of ZSM-5 per hour. The MPDA used was a commercial product obtainable from DuPont de Nemours under the trade name Dytek A. The product from the cyclization reactor was kept in the gas phase and conveyed directly to a second reactor. This reactor contained 12 g of a alehydrogenation catalyst composed of Pd and $MgCl_2$ on an $Al_2O_3$ support (particle size: 0.32 to 1 mm). The reaction conditions were 280° C. and about 1 bar. The condensate from the dehydrogenation reactor contained, after a reaction time of 220 hours, 99.1 percent of 3-picoline and 0.9 percent of MPI (by gas chromatography). A deactivation of the two catalysts over the reaction time was not observed.

EXAMPLE 1d

2-Methyl-1,5-daiminopentane (MPDA) to 3-picoline Continuously in Two Stages

A reactor (13 mm φ) was charged with 3 g of $SiO_2$/$Al_2O_3$ granules (Si-HP-87-069 T from Engelhard) having a particle size of 0.315 to 1 mm. MPDA was vaporized and, together with a carrier gas stream of 15 ml/minute of $H_2$, passed at a pressure of about 1 bar and a reactor temperature of 320° C. over the catalyst and cyclized to form MPI. The MPDA used was a commercial product obtainable from DuPont de Nemours under the trade name Dytek A. The product from the cyclization reactor was kept in the gas phase and conveyed directly to a second reactor. This reactor contained 3 g of the dehydrogenation catalyst from Example 18 of WO 94/22824 (particle size: 0.32 to 1 mm). The reactor temperature was 280° C., the pressure was 1 bar. During the course of the experiment, the starting material MPDA was converted into MPI and then into a crude product (3-MP crude) consisting of a mixture having the following composition: 74.9 percent of MPI, 13.9 percent of MPDA, 5.1 percent of organic impurities (mainly methylcyclopentanediamines) and 6.1 percent of water. The results together with the associated MHSVs (MHSV based on Reactor 1) are shown in the following table:

| Starting Material | MHSV [1/h] | GC % by area PIC | GC % by area MPI | Running Time [h] | Deactivation [PIC %/h] |
|---|---|---|---|---|---|
| Dytek A | 2.1 | 99.7 | — | 71 | 0 |
| Dytek A | 3.15 | 99.6 | 0.2 | 25 | 0 |
| Dytek A | 4.2 | 98.6 | 1.4 | 48 | 0 |
| MPI | 4.1 | 95.2 | 3.8 | 3 | — |
| MPI | 3.52 | 98.6 | 0.6 | 92 | 0 |
| 3-MP crude | 4.2 | 93.9 | 1.5 | 170 | 0.0172 |

EXAMPLE 2a

Ammonoxidation of 3-picoline to 3-cyanopyridine 36.4 g of vanadium pentoxide, 48.0 g of titanium dioxide, 197.2 g of zirconium dioxide and 0.42 g of molybdenum trioxide were milled in a ball mill. The molar ratio of $V_2O_5$:$TiO_2$:$ZrO_2$ was 1:3:8, respectively, and the $MoO_3$ content was 1.15 percent by weight, based on $V_2O_5$. Pellets having dimensions of 5×5 mm were formed from the mixture. These were subjected to a heat treatment (100° to 120° C., for 6 hours in a stream of air). 60 cm³ (82 g) of the catalyst thus pretreated were placed in a tube reactor (stainless steel, internal diameter 20 mm, length 1,000 mm). At a catalyst bed temperature of 330° C., a mixture of 3-picoline, air and ammonia was then passed over the catalyst at a feed rate of (g per 1 of catalyst per hour=gl$^{-1}$ lh$^{-1}$) 84 gl$^{-1}$h$^{-1}$ of 3-picoline; 2,000 gl$^{-1}$h$^{-1}$ of air; and 9.92 gl$^{-1}$h$^{-1}$ of ammonia. The molar composition of the feed gas was 3-picoline:$O_2$:$NH_3$=1:40:1.3. Accordingly, 25.5 g of 3-picoline was passed over the catalyst in 10 hours. The conversion was 100 percent. 26.8 g of 3-cyanopyridine was obtained, which corresponds to a yield of 95.0 percent.

EXAMPLE 2b

Ammonoxidation of 3-picoline to 3-cyanopyridine
(in a Multitube Reactor Without Additional Thermal Treatment of the Catalyst)

11.67 kg of vanadium pentoxide, 25.12 kg of titanium oxide as metatitanic acid, 63.22 kg of zirconium oxide and 1124 g of molybdenum trioxide (as ammonium paramolybdate) were milled in a ball mill. The molar ratio of $V_2O_5$:$TiO_2$:$ZrO_2$ was 1:4:8, respectively, and the $MoO_3$ content was 1.13 percent, based on $V_2O_5$. Pellets having dimensions of 6×6 mm were formed from the mixture. These were subjected to a heat treatment (100° to 120° C., for 6 hours in a stream of air).

A quantity (72 kg, 53 liters) was placed in a tube reactor (stainless steel, internal diameter 21 mm, length 3,000 mm, number of tubes 51). At a catalyst bed temperature of 340° C., a mixture of 3-picoline, air, recirculated waste gas and ammonia was then passed over the catalyst at a feed rate of (g per 1 of catalyst per hour=gl$^{-1}$h$^{-1}$) 3.1 kgh$^{-1}$ of 3-picoline (60 gl$^{-1}$h$^{-1}$), 7.6 kgh$^{-1}$ of air, 67.0 kgh$^{-1}$ of waste gas, and 0.84 kgh$^{-1}$ of ammonia. The molar composition of the feed gas was 3-picoline:$O_2$:$NH_3$=1:1.9:1.5, respectively. Accordingly, 1,860 kg of 3-picoline was passed over the catalyst in 600 hours. 1,880 kg of 3-cyanopyridine was obtained, which corresponds to a yield of 90.4 percent.

EXAMPLE 2c

Ammonoxidation of 3-picoline to 3-cyanopyridine
(in a Single-tube Reactor with Additional Thermal Treatment of the Catalyst)

A quantity of the catalyst obtained in Example 2b (135 cm³, 160 g) was treated thermally at 620° C. for 6 hours in a stream of air. This was subsequently placed in a tube reactor (internal diameter 21 mm, length 1,000 mm). At a catalyst bed temperature of 375° C., a mixture of 3-picoline, air, nitrogen and ammonia was passed over the catalyst. The feed rate was 11 gh$^{-1}$ of 3-picoline (corresponds to 81 g of picoline per liter of catalyst per hour), 30 lh$^{-1}$ of air, 285 lh$^{-1}$ of nitrogen, and 4 gh$^{-1}$ of ammonia, corresponding to a molar ratio of 3-picoline:$O_2$:$NH_3$ of 1:2:2.6, respectively. After 24 hours, 264 g of picoline had been passed over the catalyst bed. The conversion was 99 percent. 261 g of 3-cyanopyridine was obtained, viz. a yield of 89 percent. The productivity of 3-cyanopyridine was 80 gl$^{-1}$h$^{-1}$.

EXAMPLE 2d

Ammonoxidation of 3-picoline to 3-cyanopyridine
(in a Single-tube Reactor with Smaller Pellets and Higher Picoline Productivity)

Pellets having dimensions between 3 and 4 mm were formed from the catalyst obtained in Example 2b. A quantity (1 liter, 1.5 kg) was placed in a tube reactor (stainless steel, internal diameter 21 mm, length 3,000 mm). A mixture of 3-picoline, air, nitrogen and ammonia was passed over the catalyst at a catalyst bed temperature of 353° C. The feed rate was 96 gh$^{-1}$ of 3-picoline (corresponds to 96 g of picoline per liter of catalyst per hour), 210 lh$^{-1}$ of air, 1,340 lh$^{-1}$ of nitrogen, and 60 gh$^{-1}$ of ammonia. Accordingly, 2,305 g of 3-picoline were passed over the catalyst bed in 24 hours. 2,380 g of 3-cyanopyridine was obtained, which corresponds to a yield of 90 percent. The 3-picoline conversion was 97.5 percent.

| | Catalyst Composition | | | | Gas feed in g/Letter of catalyst/h | | | | | 3-Cyanopyridine | |
| | % by weight based on | | | | | | | | | | |
| | in mol | | | $V_2O_5$ | Air or air | | | Temperature | Conversion | Molar | Productivity in g/l of |
| Example | $V_2O_5$ | $TiO_2$ | $ZrO_2$ | $MoO_3$ | 3-Pic | mixture | Ammonia | °C. | % | Yield % | catalyst/h |
|---|---|---|---|---|---|---|---|---|---|---|---|
| 2a | 1 | 3 | 8 | 1.15 | 84 | 1667 | 9.9 | 330° | 100 | 95 | 89.3 |
| 2b | 1 | 4 | 8 | 1.13 | 60 | 1407 | 15.8 | 340° | 100 | 90.4 | 60.7 |
| 2c | 1 | 4 | 8 | 1.13 | 81 | 1944 | 29.6 | 375° | 99 | 89.0 | 80.6 |
| 2d | 1 | 4 | 8 | 1.13 | 96 | 1550 | 60.0 | 353° | 97.5 | 90.0 | 96.6 |

Oxidative ammonolysis of picoline (3-Pic)

EXAMPLE 3a

Preparation of Nicotinamide (NA) from 3-cyanopyridine

In a cascade comprising a 1.125 l reactor and two 0.375 l reactors, a 10 percent strength solution of 3-cyanopyridine was converted into NA. At a throughput rate of 300 ml/hr of stating material solution, cyanopyridine was converted quantitatively into NA; the first reactor contained 45 g of immobilized microorganisms. The biocatalyst remained in the respective reactors during the entire experiment. The biocatalyst contained immobilized microorganisms of the species *Rhodococcus rhodochrous* J1.

The reaction occurred at a temperature of 25°±1° C. and a pH of from 8 to 8.5. The pH was set using phosphoric acid and sodium hydroxide solution. In this experiment, the reaction of cyanopyridine proceeded for 2,400 hours, without the product stream containing more than 0.05 percent of cyanopyridine, which corresponds to a conversion of >99.5 percent. The activity of the catalyst was exhausted after this time.

Product solution containing from 14 to 15 percent of NA was filtered through a 0.2 µm sterilizing filter. The clear product solution obtained was subsequently evaporated to dryness. The product obtained contained >99.7 percent of NA (titration) and corresponded to pharmaceutical quality.

EXAMPLE 3b

Preparation of NA from 3-cyanopyridine

In a cascade comprising a 150 l reactor and two 45 l reactors, a 15 percent strength solution of 3-cyanopyridine was converted into NA. At a throughput rate of 25 l/h of starting material solution, cyanopyridine was quantitatively converted into NA; the first reactor contained 6 kg of immobilized microorganisms (dry weight) and the two further reactors each contained 0.9 kg (dry weight) of immobilized microorganisms. The biocatalyst remained in the respective reactors during the entire experiment. The biocatalyst contained immobilized microorganisms of the species *Rhodococcus rhodochrous* J1.

The reaction occurred at a temperature of 24°±2° C. and a pH of from 7 to 8.5. The pH was set using phosphoric acid and sodium hydroxide solution, with potassium dihydrogen phosphate also being used for buffering (1 to 3 mg/l).

In this experiment, the reaction of cyanopyridine proceeded for 1,800 hours, without the product stream containing more than 0.1 percent of cyanopyridine, which corresponds to a conversion of >99.0 percent. The activity of the biocatalyst was exhausted after this time.

Product solution containing from 18 to 20 percent of NA was subsequently purified continuously in fixed-bed adsorbers (each having a volume of 15.7 l), with from 0.5 to 4 percent of activated carbon (based on amount of product) and from 0.5 to 2 percent of Amberlite XAD2 being used.

Additionally purified NA solution was subsequently filtered continuously. Use was made of a three-stage filtration system in which the product solution was first fed to a GAF filter (10 to 30 µm pore size), subsequently to a sterilizing filter (pore size 0.2 µm) and finally to an ultrafiltration (pore size from 10,000 to 30,000 Dalton).

The filtered product solution was concentrated in a falling-film evaporator to from 60 to 80 percent of NA. Water removed from the product could be recirculated to the biohydrolysis. The product was isolated in a spray dryer having an integrated fluidized bed (fluidized spray dryer).

The product obtained contained >99.7 percent of NA (titration) and corresponded to pharmaceutical quality.

What is claimed is:

1. Process for preparing nicotinamide, comprising: in a first stage
   (a) 2-methyl-1,5-diaminopentane in the gas phase at 300° to 400° C. and at 0 to 10 bar gauge pressure is converted into 3-methylpiperidine by passing it over a catalyst containing as active component at least one oxide of Al and/or Si, having at the surface a ratio of acid centers to basic centers of more than 2 and having a specific surface area of more than 40 m²/g, and, immediately afterwards, the 3-methylpiperidine is passed at 220° to 400° C. over a dehydrogenation catalyst and is converted into 3-picoline,
   then in a second stage
   (b) the 3-picoline is, in the presence of ammonia and an oxygen-containing gas, passed at 280° to 400° C. over an ammonoxidation catalyst comprising the oxides of vanadium, titanium, zirconium and molybdenum in a molar ratio of $V_2O_5$ to $TiO_2$ to $ZrO_2$ of from 1:1:2, respectively, to 1:12:25, respectively, and having a $MoO_3$ content, based on $V_2O_5$, of from 0.54 percent by weight to 2.6 percent by weight,
   and, finally, in a third stage
   (c) the resultant 3-cyanopyridine is converted by means of microorganisms of the genus Rhodococcus into nicotinamide.

2. The process according to claim 1, wherein the dehydrogenation catalyst used in the first stage is a noble metal catalyst on a support.

3. The process according to claim 2, wherein the ammonoxidation catalyst used is a catalyst composition comprising the oxides of vanadium, titanium, zirconium and molybdenum in a molar ratio of $V_2O_5$ to $TiO_2$ to $ZrO_2$ of from 1:3:4, respectively, to 1:8:16, respectively, and having a $MoO_3$ content, based on $V_2O_5$, of from 0.54 percent by weight to 1.20 percent by weight.

4. The process according to claim 3, wherein, in the second stage, 3-picoline, ammonia and the oxygen-containing gas, which is calculated as $O_2$, are passed in a molar ratio of from 1:1:1.5, respectively, to 1:8.5:60, respectively, at 310° to 380° C. over the catalyst.

5. The process according to claim 4, wherein 3-picoline, ammonia and the oxygen-containing gas, which is calculated as $O_2$, are passed in a molar ratio of from 1:1:10, respectively, to 1:4:60, respectively, at from 310° to 380° C. over the catalyst.

6. The process according to claim 5, wherein the microbiological reaction in the third stage is carried out using microorganisms of the species Rhodococcus rhodochrous or using mutants thereof.

7. The process according to claim 6, wherein immobilized microorganisms of the species Rhodococcus rhodochrous are used.

8. The process according to claim 7, wherein the microbiological reaction in the third stage is carried out at a pH of from 6 to 10 and a temperature of from 5° to 50° C.

9. The process according to claim 8, wherein the microbiological reaction in the third stage is carried out in a reactor cascade comprising from 2 to 5 connected stirred reactors.

10. The process according to claim 1, wherein the ammonoxidation catalyst used is a catalyst composition comprising the oxides of vanadium, titanium, zirconium and molybdenum in a molar ratio of Vhd $2O_5$ to $TiO_2$ to $ZrO_2$ of from 1:3:4, respectively, to 1:8:16, respectively, and having a $MoO_3$ content, based on $V_2O_5$, of from 0.54 percent by weight to 1.20 percent by weight.

11. The process according to claim 1, wherein, in the second stage, 3-picoline, ammonia and the oxygen-containing gas, which is calculated as $O_2$, are passed in a molar ratio of from 1:1:1.5, respectively, to 1:8.5:60, respectively, at 310° to 380° C. over the catalyst.

12. The process according to claim 1, wherein the microbiological reaction in the third stage is carried out using microorganisms of the species Rhodococcus rhodochrous or using mutants thereof.

13. The process according to claim 1, wherein the microbiological reaction in the third stage is carried out at a pH of from 6 to 10 and a temperature of from 5° to 50° C.

14. The process according to claim 1, wherein the microbiological reaction in the third stage is carried out in a reactor cascade comprising from 2 to 5 connected stirred reactors.

15. Process for preparing nicotinamide, comprising passing 3-picoline, in the presence of ammonia and an oxygen-containing gas, at 280° to 400° C. over an ammonoxidation catalyst comprising the oxides of vanadium, titanium, zirconium and molybdenum in a molar ratio of $V_2O_5$ to $TiO_2$ to $ZrO_2$ of from 1:1:2, respectively, to 1:12:25, respectively, and having a $MoO_3$ content, based on $V_2O_5$, of from 0.54 percent by weight to 2.6 percent by weight, and subsequently converting the resultant 3-cyanopyridine by means of microorganisms of the genus Rhodococcus into nicotinamide.

16. The process according to claim 15, wherein the ammonoxidation catalyst used is a catalyst composition comprising the oxides of vanadium, titanium, zirconium and molybdenum in a molar ratio of $V_2O_5$ to $TiO_2$ to $ZrO_2$ of from 1:3:4, respectively, to 1:8:16, respectively, and having a $MoO_3$ content, based on $V_2O_5$, of from 0.54 percent by weight to 1.20 percent by weight.

17. The process according to claim 16, wherein 3-picoline, ammonia and the oxygen-containing gas, which is calculated as $O_2$, are passed in a molar ratio of from 1:1:1.5, respectively, to 1:8.5:60, respectively, at 310° to 380° C. over the catalyst.

18. The process according to claim 17, wherein 3-picoline, ammonia and the oxygen-containing gas, which is calculated as $O_2$, are passed in a molar ratio of from 1:1:10, respectively, to 1:4:60, respectively, over the catalyst.

19. The process according to claim 18, wherein the microbiological reaction is carried out using microorganisms of the species Rhodococcus rhodochrous or using mutants thereof.

20. The process according to claim 19, wherein immobilized microorganisms of the species Rhodococcus rhodochrous are used.

21. The process according to claim 20, wherein the microbiological reaction is carried out at a pH of from 6 to 10 and a temperature of from 5° to 50° C.

22. The process according to claim 21, wherein the microbiological reaction is carried out in a reactor cascade comprising from 2 to 5 connected stirred reactors.

23. The process according to claim 15, wherein 3-picoline, ammonia and the oxygen-containing gas, which is calculated as $O_2$, are passed in a molar ratio of from 1:1:1.5, respectively, to 1:8.5:60, respectively, at 310° to 380° C. over the catalyst.

24. The process according to claim 15, wherein the microbiological reaction is carded out using microorganisms of the species Rhodococcus rhodochrous or using mutants thereof.

25. The process according to claim 15, wherein the microbiological reaction is carried out at a pH of from 6 to 10 and a temperature of from 5° to 50° C.

26. The process according to claim 15, wherein the microbiological reaction is carried out in a reactor cascade comprising from 2 to 5 connected stirred reactors.

* * * * *